US00PP22954P2

(12) United States Plant Patent
Zuidgeest

(10) Patent No.: US PP22,954 P2
(45) Date of Patent: Aug. 14, 2012

(54) ***ALBUCA* PLANT NAMED 'FRIZZLE SIZZLE'**

(50) Latin Name: *Albuca spiralis*
Varietal Denomination: Frizzle Sizzle

(75) Inventor: Gerardus Adrianus Maria Zuidgeest, Honselersdijk (NL)

(73) Assignee: Zuidgeest Honselersdijk v.o.f., Honselersdijk (NL)

( * ) Notice: Subject to any disclaimer, the term of this patent is extended or adjusted under 35 U.S.C. 154(b) by 0 days.

(21) Appl. No.: 13/200,529

(22) Filed: Sep. 23, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Albuca* plant named 'Frizzle Sizzle', characterized by its upright plant habit; sturdy and strong plants; relatively rapid bulb development; short, spiraling leaves; and fragrant flowers.

2 Drawing Sheets

Botanical designation: *Albuca spiralis*.
Cultivar denomination: 'FRIZZLE SIZZLE'.

BACKGROUND OF THE INVENTION

The present invention relates to a new and distinct cultivar of *Albuca* plant, botanically known as *Albuca spiralis* and hereinafter referred to by the name 'Frizzle Sizzle'.

The new *Albuca* plant is a product of a planned breeding program conducted by the Inventor in Honselersdijk, The Netherlands. The objective of the breeding program is to create new *Albuca* plants with strongly spiraling leaves.

The new *Albuca* plant originated from a self-pollination made by the Inventor in Honselersdijk, The Netherlands in May, 2005 of an unnamed selection of *Albuca spiralis*, not patented. The new *Albuca* plant was discovered and selected by the Inventor as a single flowering plant from within the progeny of the stated self-pollination in a controlled greenhouse environment in Honselersdijk, The Netherlands in December, 2007.

Asexual reproduction of the new *Albuca* plant by in vitro propagation in a controlled environment in Honselersdijk, The Netherlands since November, 2008 has shown that the unique features of this new *Albuca* plant are stable and reproduced true to type in successive generations.

SUMMARY OF THE INVENTION

Plants of the new *Albuca* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Frizzle Sizzle'. These characteristics in combination distinguish 'Frizzle Sizzle' as a new and distinct *Albuca* plant:

1. Upright plant habit.
2. Sturdy and strong plants.
3. Relatively rapid bulb development.
4. Short, spiraling leaves.
5. Fragrant flowers.

Plants of the new *Albuca* can be compared to plants of the parent selection. Plants of the new *Albuca* differ from plants of the parent selection in the following characteristics:

1. Bulbs of plants of the new *Albuca* develop faster than bulbs of plants of the parent selection.
2. Leaves of plants of the new *Albuca* are thicker and more spiraling than leaves of plants of the parent selection.

Plants of the new *Albuca* can be compared to plants of other unnamed selections of *Albuca spiralis*, not patented. In side-by-side comparisons conducted in Honselersdijk, The Netherlands, plants of the new *Albuca* differed from plants of other unnamed selections of *Albuca spiralis* in the following characteristics:

1. Bulbs of plants of the new *Albuca* developed faster than bulbs of plants of other unnamed selections of *Albuca spiralis*.
2. Leaves of plants of the new *Albuca* were thicker and more spiraling than leaves of plants of other unnamed selections of *Albuca spiralis*.

BRIEF DESCRIPTION OF THE PHOTOGRAPHS

The accompanying colored photographs illustrate the overall appearance of the new *Albuca* plant showing the colors as true as it is reasonably possible to obtain in colored reproductions of this type. Colors in the photographs may differ slightly from the color values cited in the detailed botanical description which accurately describe the colors of the new *Albuca* plant.

The photograph on the first sheet comprises a side perspective view of a typical flowering plant of 'Frizzle Sizzle'.

The photograph on the second sheet is a close-up view of a typical flower of 'Frizzle Sizzle'.

DETAILED BOTANICAL DESCRIPTION

The aforementioned photographs and following observations and measurements describe plants of the new *Albuca* grown in a glass-covered greenhouse during the winter and spring in 10-cm containers in Honselersdijk, The Netherlands and under environmental conditions and cultural practices typical of commercial potted *Albuca* production. During the production of the plants, day temperatures ranged from 10° C. to 15° C., night temperatures ranged from 5° C. to 10° C. and light levels ranged from 2,500 to 3,500 lux. Plants were two years old when the photographs and description were taken. In the following description, color references are made to The Royal Horticultural Society Colour Chart, 1966 Edition, except where general terms of ordinary dictionary significance are used.

Botanical classification: *Albuca spiralis* 'Frizzle Sizzle'.

Parentage: Self-pollination of an unnamed selection of *Albuca spiralis*, not patented.

Propagation:

*Type*.—In vitro propagation.

*Time to produce a rooted young plant*.—About ten days.

*Root description*.—Fine, fibrous; white in color.

*Rooting habit*.—Dense.

*Bulb description*.—Shape: Flattened spherical. Height: About 4 cm. Diameter: About 8 cm. Texture: Smooth. Color: Whitish.

Plant description:

*Plant habit*.—Upright plant habit; sturdy and strong plants; vigorous growth habit and relatively rapid bulb development.

*Plant height* (*to top of foliar plane*).—About 7 cm to 8 cm.

*Plant height* (*to top of flowering stem*).—About 20 cm.

*Plant diameter* (*area of spread*).—About 15 cm.

*Flowering stems* (*peduncles*).—Length: About 20 cm. Diameter: About 8 mm. Strength: Strong. Angle: Upright. Texture: Smooth, glabrous; waxy. Color: Close to 143A.

Foliage description:

*Arrangement*.—About 24 to 28 simple leaves in basal rosette; leaves sessile; leaves strongly spiraling.

*Length*.—About 16 cm.

*Width*.—At the base, about 4 mm; at the apex, about 1 mm.

*Shape*.—Acicular.

*Apex*.—Acute.

*Margin*.—Entire; strongly spiraling.

*Texture, upper and lower surfaces*.—Smooth, glabrous; waxy.

*Venation pattern*.—Parallel.

*Color*.—Developing leaves, upper and lower surfaces: Close to 136B. Fully expanded leaves, upper and lower surfaces: Close to 136B; venation, close to 136B.

Flower description:

*Flower type and habit*.—Single star-shaped flowers arranged in a single terminal raceme; freely flowering habit with about ten to 20 flowers developing per inflorescence; flowers drooping.

*Natural flowering season*.—Flowering begins about five months after planting and plants flower throughout the summer in The Netherlands.

*Fragrance*.—Strongly fragrant; spicy.

*Flower longevity on the plant*.—About ten weeks; flowers not persistent.

*Flower longevity as a cut flower*.—About four to six weeks; flowers not persistent.

*Flower buds*.—Length: About 3 cm. Diameter: About 2.4 cm. Shape: Ovoid. Color: Close to 152D.

*Raceme height* (*including peduncle*).—About 20 cm.

*Raceme diameter*.—About 15 cm.

*Flower diameter*.—About 1.5 cm to 1.6 cm.

*Flower depth* (*height*).—About 3 cm.

*Perianth*.—Arrangement: Six separate segments arranged in two whorls. Segment length: About 3.5 cm. Segment width: About 1.1 cm. Segment shape: Lanceolate. Segment apex: Acute. Segment base: Attenuate. Segment margin: Entire. Segment texture, upper and lower surfaces: Smooth, glabrous; waxy. Segment color: When opening, upper and lower surfaces: Close to 153A. Fully opened, upper and lower surfaces: Close to 153A; color becoming closer to 170B with development.

*Pedicels*.—Length: About 4 cm. Diameter: About 2 mm. Strength: Strong, stiff. Angle: About 45° from vertical. Texture: Smooth, glabrous; waxy. Color: Close to 175A.

*Reproductive organs*.—Stamens: Quantity per flower: Three. Filament length: About 1.3 cm. Filament color: Close to 155D. Anther shape: Oblong. Anther length: About 5 mm. Anther color: Close to 155D. Pollen amount: Abundant. Pollen color: Close to 155D and becoming close to 162A with development. Pistils: Quantity per flower: One. Pistil length: About 2.5 cm. Style length: About 1 cm. Style color: Close to 195B. Stigma color: Towards the base, close to 195A; towards the apex, close to 195B. Ovary color: Close to 195A.

*Seeds*.—Length: About 5 mm. Diameter: About 2 mm. Color: Close to 202A.

Disease/pest resistance: Plants of the new *Albuca* have not been observed to be resistant to pathogens and pests common to *Albuca*.

Temperature tolerance: Plants of the new *Albuca* have been observed to tolerate temperatures ranging from about 1° C. to about 40° C.

It is claimed:

1. A new and distinct *Albuca* plant named 'Frizzle Sizzle' as illustrated and described.

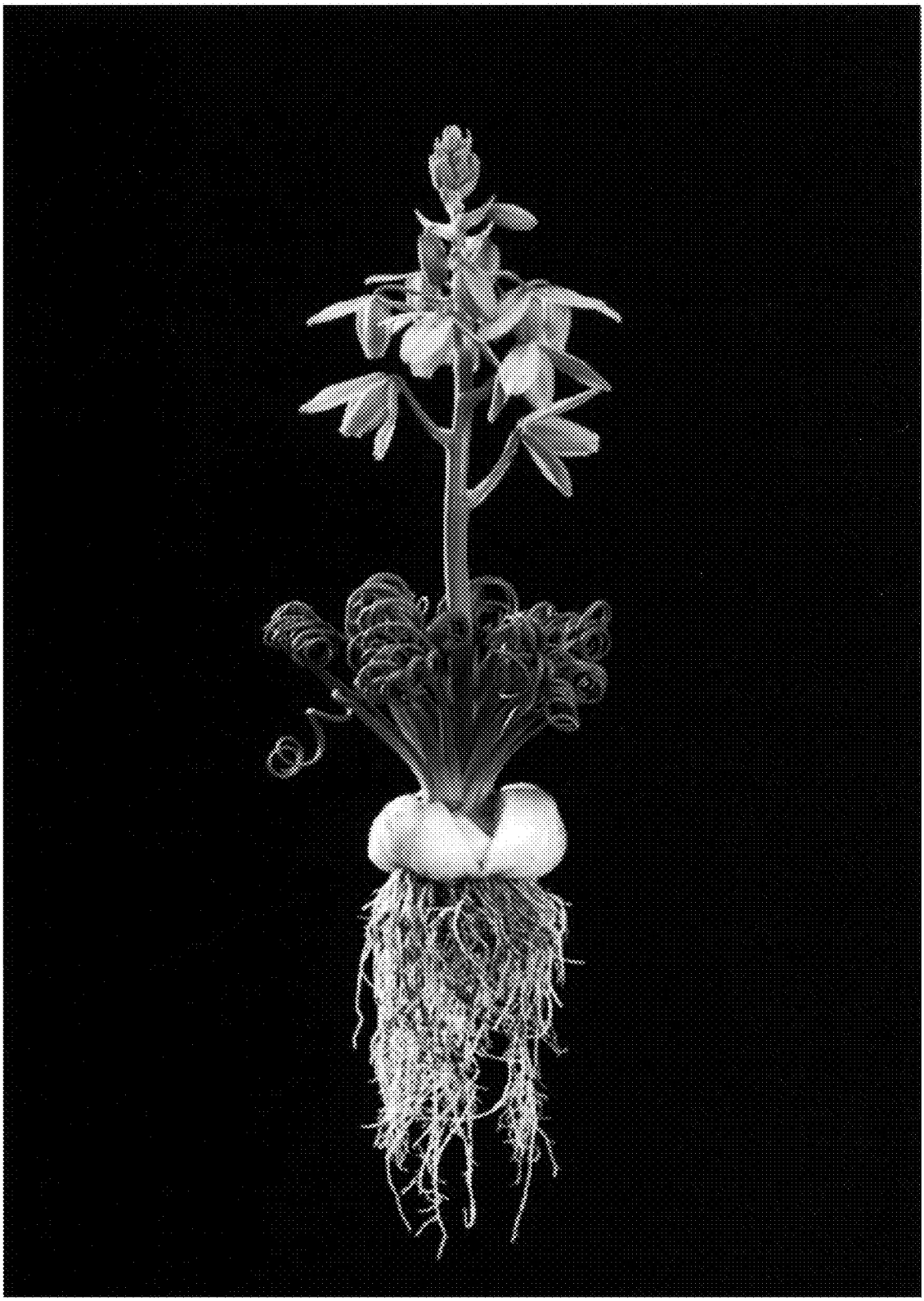

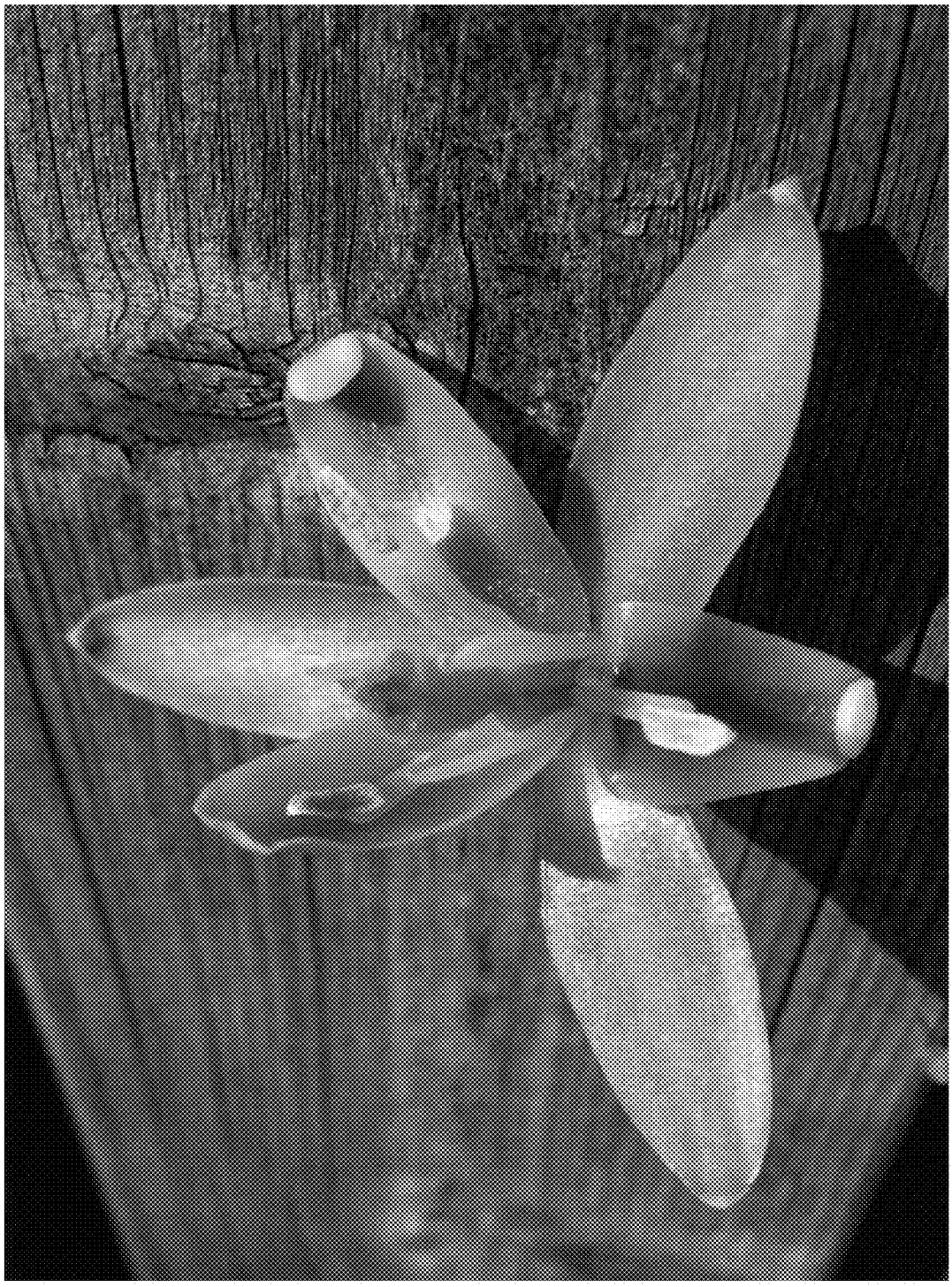

* * * * *